US008608995B2

(12) United States Patent  (10) Patent No.: US 8,608,995 B2
Sansoucy  (45) Date of Patent: Dec. 17, 2013

(54) METHOD FOR MANUFACTURING A SEPARATED TIP CATHETER

(75) Inventor: Michael R. Sansoucy, Wrentham, MA (US)

(73) Assignee: Covidien LP, Mansfield, MA (US)

( * ) Notice: Subject to any disclaimer, the term of this patent is extended or adjusted under 35 U.S.C. 154(b) by 648 days.

(21) Appl. No.: 12/823,275

(22) Filed: Jun. 25, 2010

(65) Prior Publication Data

US 2010/0327477 A1  Dec. 30, 2010

Related U.S. Application Data

(60) Provisional application No. 61/291,079, filed on Dec. 30, 2009, provisional application No. 61/221,791, filed on Jun. 30, 2009.

(51) Int. Cl.
*B29C 47/02* (2006.01)
*B29C 45/14* (2006.01)
*B28B 11/16* (2006.01)
*B28B 11/18* (2006.01)
*A61M 3/00* (2006.01)
*A61M 25/00* (2006.01)

(52) U.S. Cl.
USPC . 264/150; 264/162; 264/171.13; 264/171.26; 264/209.1; 264/209.2; 264/259; 264/264; 264/271.1; 264/279; 138/115; 138/174; 604/43; 604/284

(58) Field of Classification Search
None
See application file for complete search history.

(56) References Cited

U.S. PATENT DOCUMENTS

| | | | | |
|---|---|---|---|---|
| 2,122,335 A | * | 6/1938 | Berman et al. | 156/244.14 |
| 2,624,073 A | * | 1/1953 | Pugh | 264/171.12 |
| 5,063,018 A | * | 11/1991 | Fontirroche et al. | 264/514 |
| 5,197,976 A | * | 3/1993 | Herweck et al. | 623/1.27 |
| 5,221,256 A | * | 6/1993 | Mahurkar | 604/43 |
| 5,374,245 A | * | 12/1994 | Mahurkar | 604/43 |
| 5,800,414 A | * | 9/1998 | Cazal | 604/523 |
| 5,807,311 A | * | 9/1998 | Palestrant | 604/28 |
| 5,945,052 A | | 8/1999 | Schryver et al. | |
| 5,945,056 A | * | 8/1999 | Day et al. | 264/250 |
| 6,190,349 B1 | * | 2/2001 | Ash et al. | 604/43 |
| 6,216,960 B1 | * | 4/2001 | Aiba et al. | 239/34 |
| 6,299,596 B1 | | 10/2001 | Ding | |
| 7,393,339 B2 | * | 7/2008 | Zawacki et al. | 604/43 |
| 7,468,116 B2 | | 12/2008 | Smith et al. | |
| 7,476,352 B2 | | 1/2009 | Wilson et al. | |

(Continued)

OTHER PUBLICATIONS

International Search Report dated Sep. 1, 2010 for copending International Appln. No. PCT/US2010/040292.

(Continued)

*Primary Examiner* — Jeffrey Wollschlager
(74) *Attorney, Agent, or Firm* — John Paul Mello, Esq.

(57) ABSTRACT

A method for manufacturing a separated tip catheter having a separated tip configuration includes the steps of: extruding an extrusion material through a die to form a catheter including a catheter body having a proximal end and a distal end and defining a first lumen and a second lumen, the catheter body having a septum positioned between the first and second lumens; and feeding a strip into the die so that the strip is positioned between the first lumen and the second lumen along a length of the catheter, the strip having a first proximal section formed of a first material capable of bonding with the extrusion material and a second distal section formed of a second material incapable of bonding with the extrusion material.

18 Claims, 5 Drawing Sheets

(56) References Cited

U.S. PATENT DOCUMENTS

2003/0060807 A1* 3/2003 Tanghoj et al. ............... 604/544
2004/0059314 A1* 3/2004 Schon et al. .................. 604/544
2004/0210187 A1* 10/2004 Zawacki ......................... 604/43
2005/0261663 A1* 11/2005 Patterson et al. ............. 604/508
2006/0161100 A1* 7/2006 Hamboly ........................ 604/43
2008/0021417 A1* 1/2008 Zawacki et al. ............... 604/284

OTHER PUBLICATIONS

Extended European Search Report dated Feb. 25, 2013 in copending European Application No. 10794614.

* cited by examiner

METHOD FOR MANUFACTURING A SEPARATED TIP CATHETER

CROSS-REFERENCE TO RELATED APPLICATIONS

This application claims priority to U.S. Provisional Application Ser. No. 61/291,079 filed on Dec. 30, 2009 and U.S. Provisional Application Ser. No. 61/221,791 filed on Jun. 30, 2009. The entire contents of which is incorporated herein by reference.

BACKGROUND

1. Technical Field

The present disclosure relates generally to methods for manufacturing catheters, and, in particular, methods for manufacturing catheters having a separated tip configuration.

2. Description of the Related Art

Catheters are flexible medical devices which facilitate the withdrawal and introduction of fluids from and to body cavities, ducts, and vessels. Catheter assemblies may have particular application in a hemodialysis procedure where blood is withdrawn from a blood vessel for treatment and subsequently returned to the blood vessel for circulation. Known hemodialysis catheters include multiple bores, such as dual-lumen or triple-lumen catheters, which permit bi-directional fluid flow within the catheter whereby one lumen is dedicated for withdrawal of blood from a body vessel and the other lumen is dedicated for returning the treated blood to the vessel. During an exemplary hemodialysis procedure, a multiple lumen catheter is inserted into a body and blood is withdrawn through an arterial bore of the catheter. The removed blood is directed to a hemodialysis unit which dialyzes, or purifies, the blood to remove waste and toxins from the blood. The dialyzed blood is returned to the patient through a venous lumen of the catheter.

Catheters can be manufactured using a variety of techniques including extrusion. For example, some catheters are formed by extruding molten polymer material through a die. The polymer melt is then drawn down to form a catheter having a smaller uniform inner diameter.

SUMMARY

The present disclosure relates to a method for manufacturing a catheter having a separated tip configuration. This method includes the steps of: extruding an extrusion material through a die to form a catheter including a catheter body having a proximal end and a distal end and defining a first lumen and a second lumen, the catheter body having a septum positioned between the first and second lumens; and feeding a strip into the die so that the strip is positioned between the first lumen and the second lumen at a distal end of the catheter, the strip having a first proximal section formed of a first material capable of bonding with the extrusion material and a second distal section formed of a second material incapable of bonding with the extrusion material. The extrusion material may be a thermoplastic material. The first material of the strip may be a thermoplastic material substantially similar to the thermoplastic material used to produce the catheter and may be capable of forming a mechanical and/or chemical bond with the extrusion material. In addition, the first material is capable of forming a covalent bond with the extrusion material. The chemical bond formed between the first material and the extrusion material may have an attractive bond greater than the ionic forces of the first material and the extrusion material, i.e, an integral bond. The extrusion material may be extruded with an extruder heated before the extrusion process, and/or cooled after the extrusion process.

When the strip is fed into the die, extensions may be formed extending radially from the extrusion material. The widths of the extensions may be reduced by cutting or grinding the extensions. The extension may also be removed by melting them.

In addition, the extrusion material may be cut at a desired length after extruding it through the die. The first and second lumens of the catheter may be forming with mandrels.

The present disclosure further relates to another method for manufacturing a catheter having a separated tip configuration. This method includes the steps of extruding a polymer through a die to form a catheter including a catheter body having a proximal end and a distal end and defining a first lumen and a second lumen, the catheter body having a septum positioned between the first and second lumens; feeding a strip into the die so that the strip is positioned through the septum and between the first lumen and the second lumen at a distal end of the catheter, the strip having a first proximal section formed of a first material capable of bonding with the polymer and a second distal section formed of a second material incapable of bonding with the polymer; and cooling the polymer.

BRIEF DESCRIPTION OF THE DRAWINGS

Various embodiments of the presently disclosed catheters and manufacturing systems and methods are described herein with references to the accompanying drawings, wherein.

DETAILED DESCRIPTION OF THE EMBODIMENTS

Figure 1:
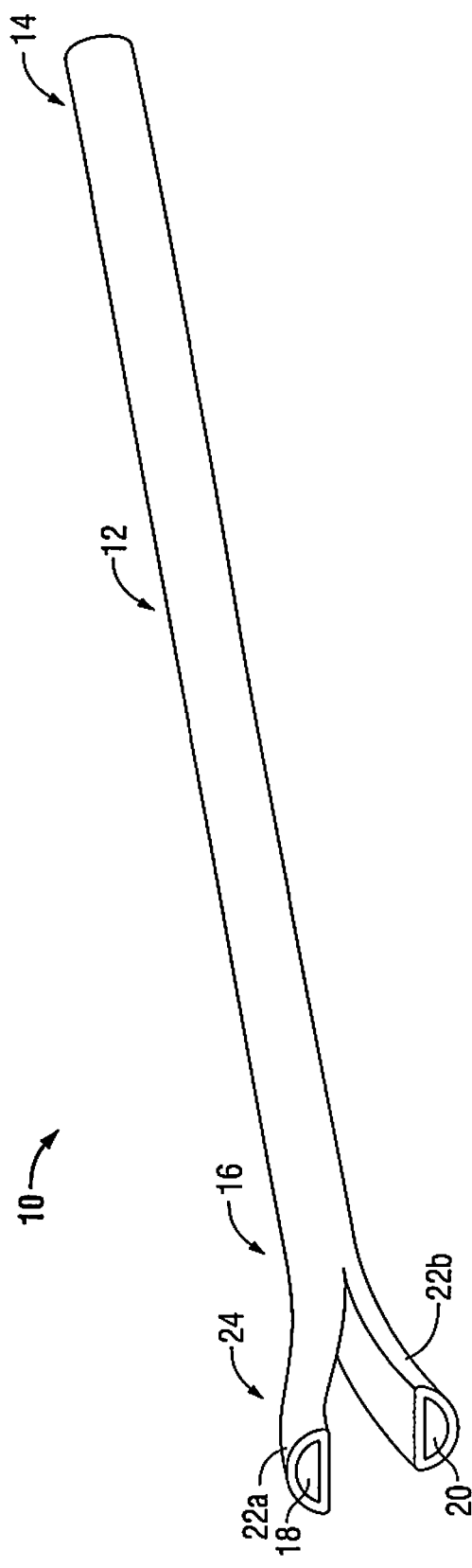
FIG. 1 is a perspective view of a catheter having a separated tip configuration.

Embodiments of the presently disclosed manufacturing systems and methods will now be described in detail with reference to the drawings wherein like reference numerals identify similar or identical elements in each of the several views. In the discussion that follows, the term "proximal" or "trailing" will refer to the portion of a structure that is closer to a user, while the term "distal" or "leading" will refer to the portion of the structure that is farther from the user.

FIG. 1 illustrates a catheter 10 having a separated tip configuration. As used herein, separated tip configuration means that the distal end of the catheter includes first and second tip members which are disconnected such that they can move or be moved in relation to each other. In general, catheter 10 includes an elongate body 12 having a proximal end portion 14 and a distal end portion 16. Elongate body 12 defines first and second lumens 18, 20 extending between proximal end portion 14 and distal end portion 16 and oriented substantially parallel to each other. In the depicted embodiment, elongate body 12 has a cylindrical shape and each of the first and second lumens 18, 20 (hereinafter also simply referred to as "lumens") has a semi-circular cross-section. Alternatively, elongate body 12 and lumens 18, 20 may have any suitable shape or configuration. Elongate body 12 further includes a septum 26 (FIG. 4) dividing first and second lumens 18, 20. Catheter 10 includes a separated tip portion 24 adjacent distal end portion 16, which includes a first member 22a and a second member 22b disconnected and separated from each other. The present disclosure describes a manufacturing process to make catheter 10.

Catheter 10 may be made of any suitable biocompatible material. In certain embodiments, catheter 10 is formed of polyurethane. To be even more specific, catheter 10 can be formed of aliphatic or aromatic polyurethane. However, catheter 10 may be made of any suitable polymer such as polyamides, polyesters, polyolefins, fluoropolymer (such as fluorinated ethylene propylene (FEP), polytetrafluoroethylene (PTFE), perfluoroalkoxy (PFA), polyvinylidene fluoride (PVDF)), polyvinyl chloride (PVC), silicones (poly-dimethyl Siloxane), and so forth, as well as combinations including at least one of the foregoing (i.e., polymer blends, copolymers, alloys and so forth).

A number of manufacturing assemblies and procedures may be employed to make catheter 10. For example, catheter 10 may be made using any suitable extrusion process. Extrusion is a manufacturing process where material is forced through an orifice of a die to produce an object having a particular cross-section. During extrusion, the material may be heated to facilitate passage of the material through the orifice of the die. Commonly extrusion materials include metals, polymers, ceramics, and concrete.

Figure 2:
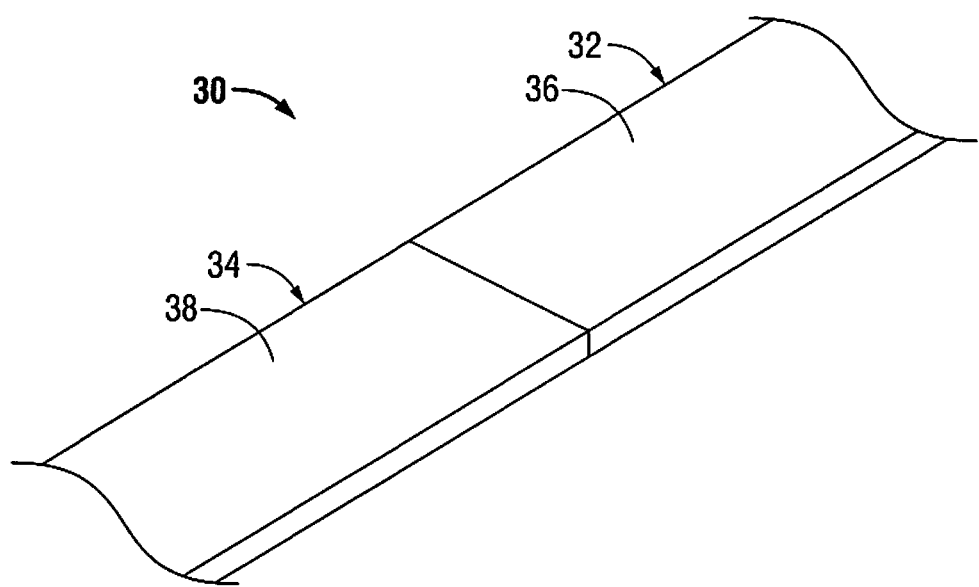
FIG. 2 is a perspective view of a portion of a strip.
Figure 3:
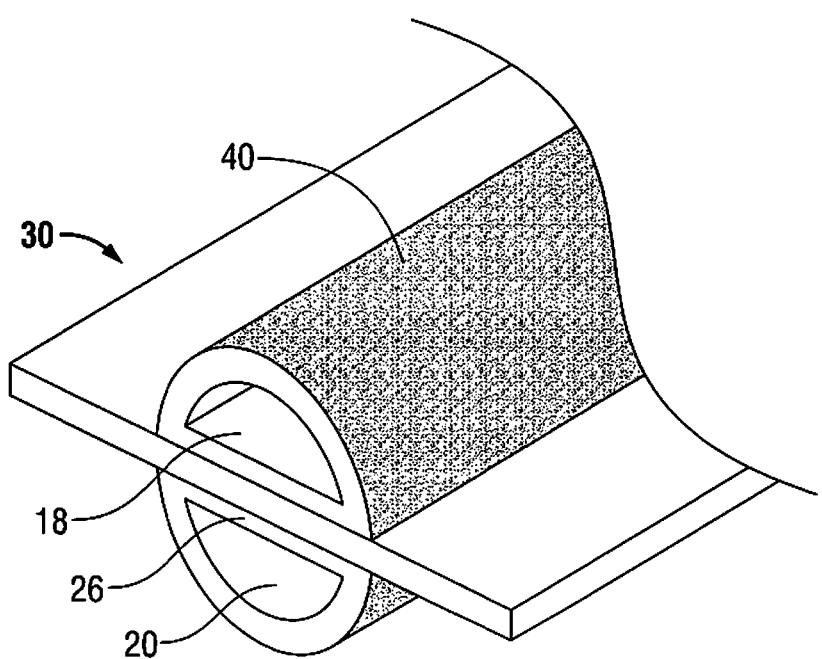
FIG. 3 is a perspective view of a portion of the strip of FIG. 2 passing through the septum of the catheter of FIG. 1.

With reference to FIGS. 2 and 3, any suitable extrusion method may be employed to form catheter 10 (FIG. 1). In most extrusion methods, a die is used to form the desired object. Any suitable die, such as a cross-head die, can be utilized to make catheter 10 (FIG. 1). Typically, the die has an orifice, which may be circular in shape, configured to form the outer surfaces or outer profile of catheter 10. In the disclosed extrusion method, a suitable extrusion material 40, such as a thermoplastic, is forced through the orifice of the die. In addition to forcing extrusion material 40 through the orifice of the die, a strip 30 is passed through the orifice of the die. Specifically, strip 30 is positioned between first and second lumens 18, 20 of catheter 10 (FIG. 1). In one embodiment, strip 30 is symmetrically inserted between lumens 18, 20 as catheter 10 forms.

As shown in FIG. 2, strip 30 may have a substantially planar configuration and includes a first section 32 and a second section 34. Second section 34 is positioned distally relative to first section 32. It is envisioned that first section 32 may be longer than second section 34 of strip 30. First section 32 is wholly or partly made of a first material 36 capable of bonding with extrusion material 40. Second section 34 is wholly or partly made of a second material 38 incapable of bonding with extrusion material 40. In an embodiment, first material 36 is substantially similar or identical to extrusion material 40. Alternatively, first section 32 may be wholly or partly made of any material capable of forming a mechanical and/or chemical bond with extrusion material 40. For example, the first material 36 may form a covalent bond with extrusion material 40. It is contemplated that both first material 36 and extrusion material 40 may be thermoplastics.

It is also envisioned that strip 30 can comprise coated sections and non-coated sections, wherein the coated sections are incapable of bonding to the extrusion material and the non-coated sections are capable of bonding to the extrusion material. For example, in one embodiment the strip can be formed of a polymer similar to the extrusion resin and have coated sections coated with PTFE, FEP, poly-(p-xylylene) polymers or polymers derived therefrom (also referred to as Parylene coatings), or other coatings generally known for their "non-stick" properties. "Non-stick" generally refers to the ability to be separated from the extrusion material.

Alternatively, second material 38 of strip 30 may be capable of forming a mechanical and/or chemical bond with extrusion material 40, and first material 36 of strip 30 may be incapable of forming a bond with extrusion material 40.

Figure 4:
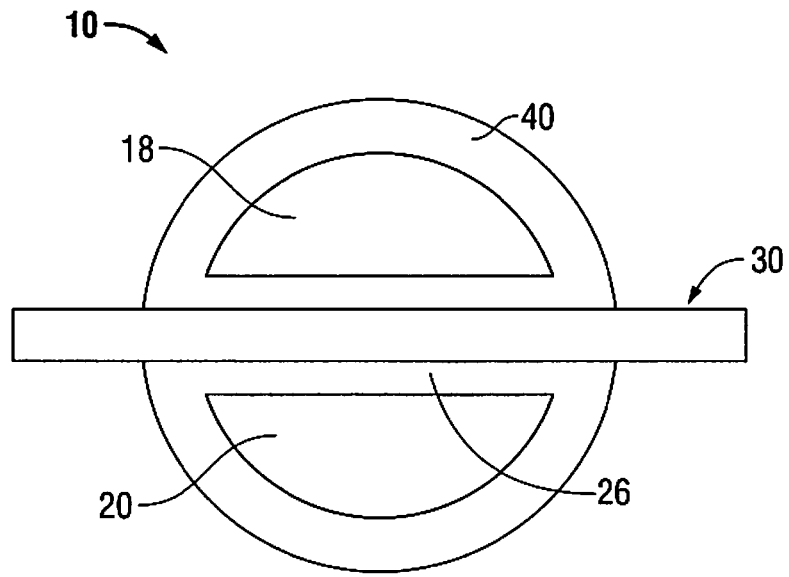
FIG. 4 is a cross-sectional view of the catheter of FIG. 1 with the strip of FIG. 2 passing through the septum of the catheter shown in FIG. 1.
Figure 5:
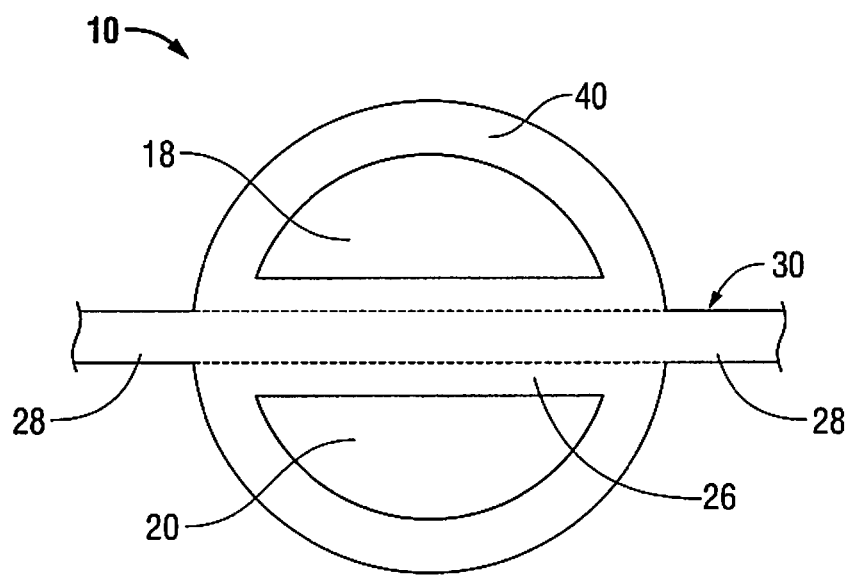
FIG. 5 is a cross-sectional view of the catheter of FIG. 1 with the strip of FIG. 2 bonded to the septum of the catheter shown in FIG. 1.

As depicted in FIGS. 4 and 5, strip 30 is disposed between first and second lumens 18, 20 during the manufacturing process. Specifically, strip 30 is inserted in septum 26 between first and second lumens 18, 20. At this juncture, first section 32 of strip 30 bonds with extrusion material 40, while second section 34 physically separates the extrusion material 40 into two parts. In this manner, a catheter 10 may be manufactured. In one exemplary method, second section 34 of strip 30 is positioned at the distal portion of extrusion material 40 to form separated tip portion 24 of catheter 10 (FIG. 1). Since second material 38 of second section 34 does not bond with extrusion material 40, second section 34 of strip 30 divides the distal portion of extrusion material 40 into first and second part 22a, 22b, thereby forming separated tip portion 24 of catheter 10. On the other hand, first section 32 bonds with the remaining portions of extrusion material 40, as shown in FIG. 5. This bond may be weak or strong (i.e., integral) depending of the specific materials chosen for catheter 10 and strip 30. In one embodiment, the bond between strip 30 and extrusion material 40 is an integral bond, i.e., a thermoplastic to thermoplastic bond having forces of attraction that are greater than or equal to the ionic forces or covalent forces. The bonding process between extrusion material 40 and strip 30 forms ears or extensions 28 extending radially from catheter 10. As discussed below in detail, ears 28 can be removed front catheter 10.

Figure 6:
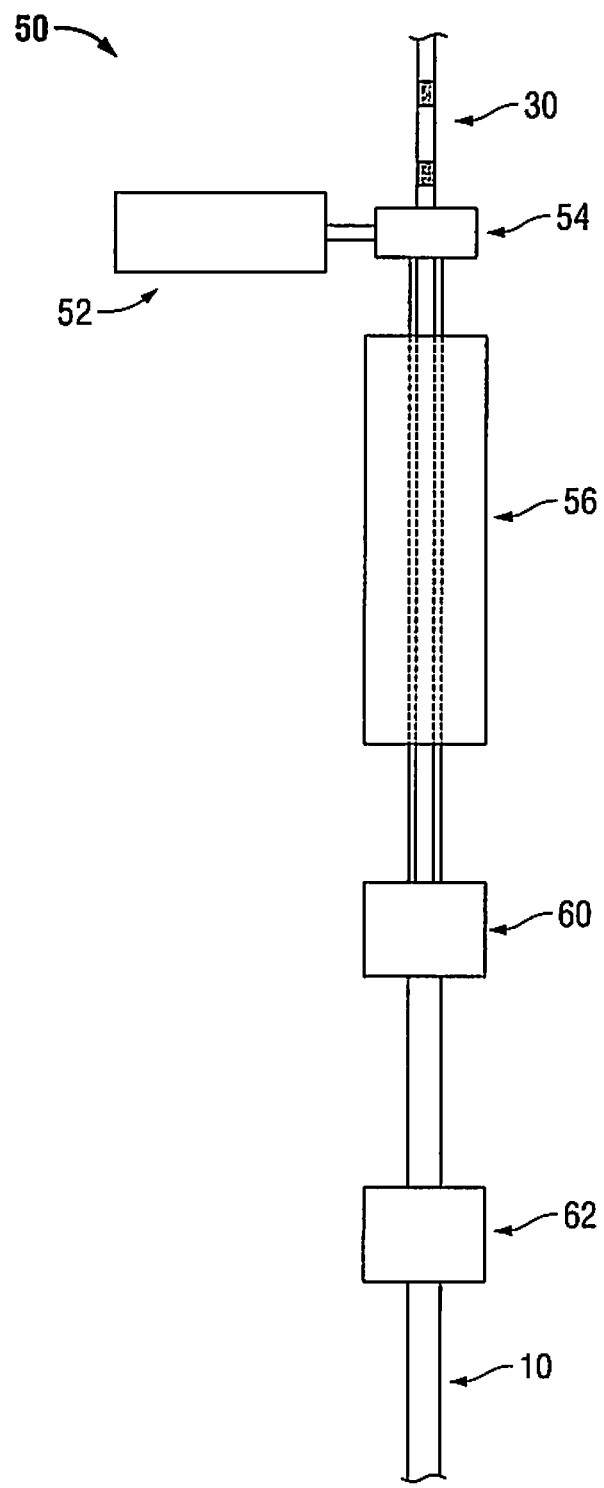
FIG. 6 is a schematic view illustrating a process to manufacture the catheter shown in FIG. 1.

FIG. 6 shows a schematic representation of an exemplary manufacturing system 50 for manufacturing catheter 10. Manufacturing system 50 includes an extruder 52, a die 54, and a cooling apparatus 56. Extruder 52 is fluidly coupled to die 54 and is configured to extrude extrusion material 40 into die 54. Extrusion material 40 is placed in extruder 52, which heats extrusion material 40. Extrusion material 40 may be heated until it melts. Then, extruder 52 forces extrusion material 40 (FIG. 3) through die 54. Die 54 has one or more orifices (not shown) configured to form the outer surfaces of catheter 10. In an embodiment, pressurized gas, such as air, is applied to the die 54 to form two substantially parallel lumens (i.e. lumens 18, 20) running lengthwise along extrusion material 40. Alternatively, mandrels (not shown) may be inserted through die 54 and into extrusion material 40 to form first and second lumens 18, 20 of catheter 10 (FIG. 1).

In addition, strip 30 is fed to the back of die 54 along septum 26 as shown in FIG. 4. In one exemplary method, second section 34 of strip 30 is positioned along extrusion material 40 so that it is placed distally relative to first section 32 of strip 30. Alternatively, first section 32 of strip 30 is positioned along extrusion material 40 so that it is placed distally with respect to second section 34 of strip 30. During this manufacturing process, first material 36 of first section 32 mechanically and/or chemically bonds with extrusion material 40 as depicted in FIG. 5. Optionally, catheter 10 can be cut to a desired length after it exits die 54.

Figure 7:
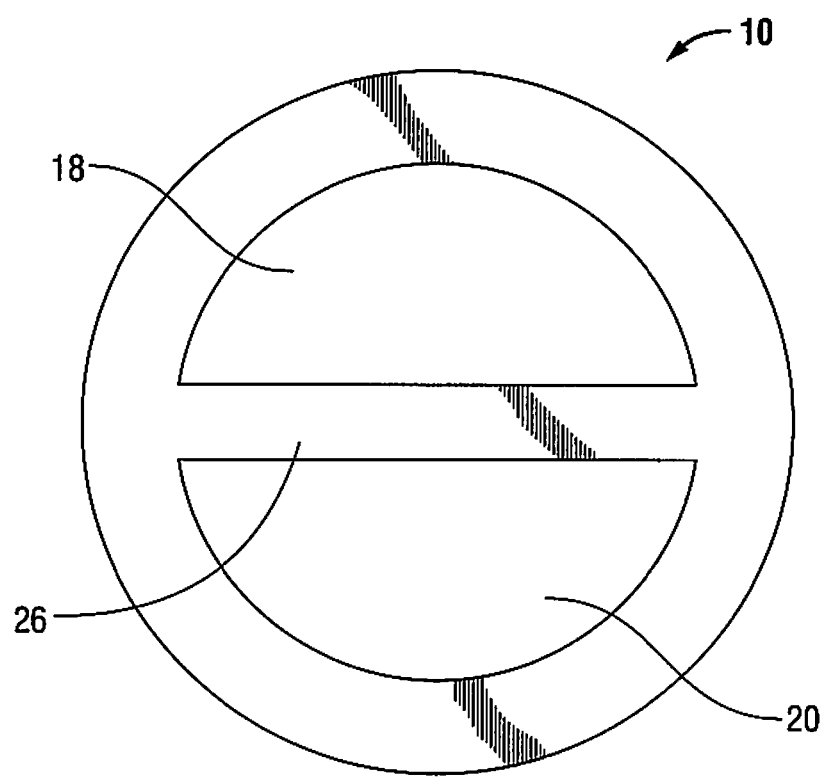
FIG. 7 is a cross-sectional view of the catheter of FIG. 1.

After passing extrusion material 40 and strip 30 through die 54, extrusion material 40 is passed through a cooling apparatus 56. Cooling apparatus 56 cools extrusion material 40 and solidifies it to form a catheter, e.g., catheter 10 (FIG. 1). A "puller" is commonly placed after the cooling apparatus to pull the extrudate at a constant rate. Optionally, catheter 10 can be passed through a cutter or ear cutter 60 which cuts, grinds, and/or performs any other suitable process to reduce the width of ears 28 of catheter 10 (See FIG. 4). After this optional step, catheter 10 is passed through a former 62, which is capable of removing ears 28. Alternatively, catheter 10 can be sent through a heated die capable of melting ears 28 to provide catheter 10 with a smooth surface, as shown in FIG. 7. In yet another embodiment, the catheter can be cut to length and then subjected to the finishing processes described above, as well as others. For example, in one embodiment catheter 10 can be cut to length after being passed through ear-cutter 60. Thereafter, catheter 10 can be inserted into heat-shrink tubing and subjected to a heating process capable of shrinking the heat-shrink tubing around the outer diameter of the catheter and melting at least a portion of the catheter 10 material. The catheter 10 can then be cooled below the catheter material's melting point and the heat-shrink tubing can be removed. Once removed, catheter 10 will comprise an outer diameter that is mostly-free or completely free of ears. However, it is to be understood that it is envisioned that catheter 10 may be subject to any finishing process suitable for providing catheter 10 with a smooth outer surface, including, but not limited to, those discussed herein.

Once the catheter 10 is cut to length, the portion of the extrusion material 40 that was in contact with the second section 34 of strip 30 will not bond together and will form the first and second members 22a, 22b of the separated tip portion 24 adjacent the distal end portion 16. If necessary, the second section 34 of the strip 30 can be removed from catheter 10.

Although the specific features of the disclosure are shown in some drawings and not in others, this is for convenience only as each feature may be combined with any or all of the other features in accordance with the disclosure.

It will be understood that various modifications may be made to the embodiments of the presently disclosed clamping assemblies. Therefore, the above description should not be construed as limiting, but merely as exemplifications of embodiments. Those skilled in the art will envision other modifications within the scope and spirit of the present disclosure.

What is claimed is:

1. A method for manufacturing a catheter having a separated tip configuration, comprising the steps of:
    extruding an extrusion material of thermoplastic material through a die to form a catheter including a catheter body having a proximal end and a distal end and defining a first lumen and a second lumen, the catheter body having a septum positioned between the first and second lumens; and
    feeding a strip into the die so that the strip is positioned between the first lumen and the second lumen along a length of the catheter, the strip having a first non-coated proximal section formed of a first material comprising the thermoplastic material and capable of bonding with the extrusion material, and a second distal section formed of a second material incapable of bonding with the extrusion material.

2. The method according to claim 1, wherein the first material is capable of forming a mechanical bond with the extrusion material.

3. The method according to claim 1, wherein the step of feeding the strip into the die functions to define a separated tip portion having a first member communicating with the first lumen and a second tip member communicating with the second lumen.

4. The method according to claim 3, wherein the first material is capable of forming a covalent bond with the extrusion material.

5. The method according to claim 3, wherein the first material is capable of forming a chemical bond between the first material and the extrusion material having an attractive bond greater than the ionic forces of the first material and the extrusion material.

6. The method according to claim 1, wherein the first material and the extrusion material are capable of forming an integral bond.

7. The method according to claim 1, further comprising the step of extruding the extrusion material with an extruder.

8. The method according to claim 1, further comprising the step of heating the extrusion material before extruding the extrusion material through the die.

9. The method according to claim 8, further comprising the step of cooling the extrusion material after extruding the extrusion material through the die.

10. The method according to claim 1, wherein the step of feeding the strip into the die includes forming extensions extending radially from the extrusion material.

11. The method according to claim 10, further comprising the step of reducing the widths of the extensions.

12. The method according to claim 11, wherein the step of reducing the widths of the extensions includes cutting the extensions.

13. The method according to claim 11, wherein the step of reducing the widths of the extensions includes grinding the extensions.

14. The method according to claim 10, further comprising the step of removing the extensions from the extrusion material.

15. The method according to claim 14, wherein the step of removing the extensions from the extrusion material includes melting the extensions.

16. The method according to claim 1, further comprising the step of cutting the extrusion material at a desired length after extruding the extrusion material through the die.

17. The method according to claim 1, wherein the step of extruding the extrusion material through the die to form the catheter includes forming the first and second lumens of the catheter with mandrels.

18. A method for manufacturing a catheter having a separated tip configuration, comprising the steps of:
    extruding a polymer through a die to form a catheter including a catheter body having a proximal end and a distal end and defining a first lumen and a second lumen, the catheter body having a septum positioned between the first and second lumens;
    feeding a strip into the die so that the strip is positioned through the septum and between the first lumen and the second lumen along a length of the catheter, the strip having a first non-coated proximal section formed of a first material comprising the polymer used to form the catheter and capable of bonding with the polymer, and a second distal section formed of a second material incapable of bonding with the polymer; and
    cooling the polymer.

* * * * *